(12) United States Patent
Ruwwe et al.

(10) Patent No.: US 7,297,812 B2
(45) Date of Patent: Nov. 20, 2007

(54) PROCESS FOR PREPARING UNSATURATED, CYCLIC ORTHOESTERS

(75) Inventors: Johannes Ruwwe, Niederkassel (DE); Jutta Hessing, Dorsten (DE); Kerstin Bodmann, Baltschieder (CH)

(73) Assignee: Degussa AG, Duesseldorf (DE)

( * ) Notice: Subject to any disclaimer, the term of this patent is extended or adjusted under 35 U.S.C. 154(b) by 28 days.

(21) Appl. No.: 11/408,102

(22) Filed: Apr. 21, 2006

(65) Prior Publication Data

US 2006/0281930 A1 Dec. 14, 2006

(30) Foreign Application Priority Data

Apr. 22, 2005 (DE) .................... 10 2005 018 909

(51) Int. Cl.
*C07C 69/63* (2006.01)

(52) U.S. Cl. .................................... 560/228

(58) Field of Classification Search .................... None
See application file for complete search history.

(56) References Cited

U.S. PATENT DOCUMENTS 5,171,866 A * 12/1992 Khouri ....................... 549/449

FOREIGN PATENT DOCUMENTS

| EP | 0 496 116 A1 | 7/1992 |
| EP | 0 731 141 A1 | 9/1996 |

OTHER PUBLICATIONS

A. S. Shevchuk, et al., "Isolation and Purification of Dioxolanylmethyl Methacrylates", Russian Journal of Applied Chemistry, vol. 73, No. 5, XP-008067010, 2000, pp. 853-855.

* cited by examiner

*Primary Examiner*—Karl Puttlitz
(74) *Attorney, Agent, or Firm*—Oblon, Spivak, McClelland, Maier & Neustadt, P.C.

(57) ABSTRACT

An unsaturated, cyclic orthoester is prepared by reacting an unsaturated carboxylic acid with glycidol, thereby obtaining a reaction mixture; and adding an orthoester to the reaction mixture, thereby obtaining said unsaturated, cyclic orthoester.

20 Claims, No Drawings

PROCESS FOR PREPARING UNSATURATED, CYCLIC ORTHOESTERS

BACKGROUND OF THE INVENTION

1. Field of the Invention

The present invention relates to a process for preparing unsaturated, cyclic orthoesters.

2. Discussion of the Background

The unsaturated, cyclic orthoesters find use in the preparation of various polymer blends which comprise polymers which are generally regarded as immiscible with one another, for example polyesters and polyolefins (EP 0 496 116 A1, EP 0 499 717 A1). EP 0 519 642 describes the use of a copolymer of unsaturated, cyclic orthoesters in a polymeric blend consisting of polyphenylene ether and polyester. These copolymers based on unsaturated, cyclic orthoesters enable compatibility between these two polymer types.

The unsaturated, cyclic orthoesters are prepared according to previously described processes by first cyclizing glycerol with an orthoester (see reaction 1) and reacting the resulting hydroxy orthoester with acryloyl chloride or methacryloyl chloride in the presence of a base to give the target compound (see reaction 2). 4-Acryloyloxymethyl-2-methoxy-2-methyl-1,3-dioxolane ((2-methoxy-2-methyl-1,3-dioxolan-4-yl)methyl acrylate, MMDA) can, for example, be prepared in this way when the substituent R of the acid chloride is a hydrogen atom.

Reaction 1:

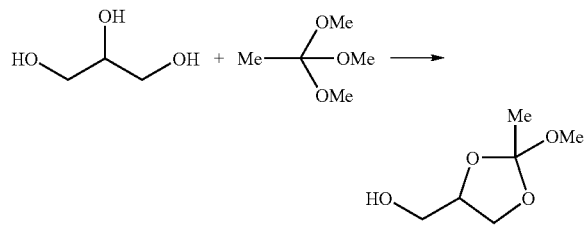

Reaction 2:

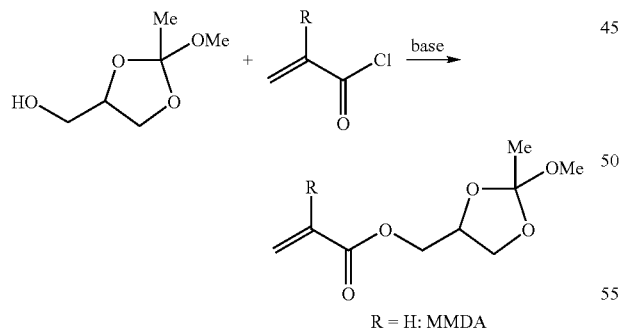

R = H: MMDA

EP 0 471 222, EP 0 475 039 and EP 0 475 040 describe, for example, the reaction of glycerol (1,2,3-propanetriol) with methyl orthoacetate in methylene chloride in the presence of p toluenesulfonic acid according to reaction 1.

The reaction of the cyclized orthoester with acryloyl chloride or methacryloyl chloride in methylene chloride and in the presence of triethylamine according to reaction 2 is described, inter alia, by EP 0 496 116, EP 0 499 717, EP 0 519 642 and EP 0 731 141.

SUMMARY OF THE INVENTION

It is an object of the present invention to provide a process for preparing unsaturated, cyclic orthoesters, which features a good space-time yield and the use of inexpensive, commercially available raw materials.

This and other objects have been achieved by the present invention the first embodiment of which includes a process for preparing an unsaturated, cyclic orthoester, comprising:
in a first process stage, reacting an unsaturated carboxylic acid with glycidol, thereby obtaining a reaction mixture; and
in a second process stage, adding an orthoester to the reaction mixture, thereby obtaining said unsaturated, cyclic orthoester.

DETAILED DESCRIPTION OF THE INVENTION

It has been found that, surprisingly, the reaction of unsaturated carboxylic acids, for example acrylic acid or methacrylic acid, with glycidol and subsequent addition of an orthoester can afford the desired unsaturated, cyclic orthoesters, without the isolation and workup of the intermediate. The process according to the present invention has the advantage over known processes that the carboxylic acid used as a reactant, for example acrylic acid or methacrylic acid, is less expensive than the corresponding acid chloride, for example acryloyl chloride or methacryloyl chloride. A further advantage of this process according to this invention is that the two process stages can be carried out in one and the same reactor without workup of the intermediates. Previously described processes are generally carried out in methylene chloride, reaction 1 being carried out in high dilution. In contrast, the process according to the present invention can be carried out without the presence of a solvent; in particular, the process according to the present invention can be carried out without the presence of halogenated compounds, for example methylene chloride.

The present invention provides a process for preparing unsaturated, cyclic orthoesters, which comprises, in a first process stage, reacting an unsaturated carboxylic acid with glycidol and subsequently, in a second process stage, adding an orthoester to the reaction mixture.

The process according to the invention for preparing unsaturated, cyclic orthoesters features, in a first process stage, reaction of an unsaturated carboxylic acid with glycidol and subsequently, in a second process stage, addition of an orthoester to the reaction mixture.

In the context of this invention, unsaturated, cyclic orthoesters are understood to mean compounds of the structure 1

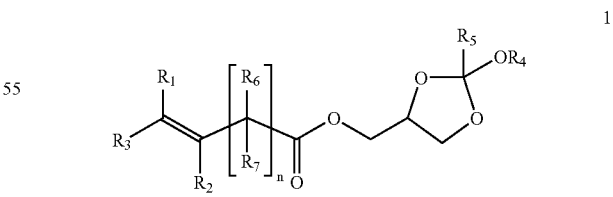

where:
$R_1$, $R_2$, $R_3$=hydrogen, alkyl or aryl group,
$R_4$=alkyl or aryl group,
$R_5$=hydrogen, alkyl or aryl group,
$R_6$, $R_7$=hydrogen or alkyl group and
n=0-10, where the alkyl or aryl groups are each substituted or unsubstituted, the substituents of the $R_1$, $R_2$, $R_3$, $R_4$, $R_5$, $R_6$ and/or $R_7$ type are identical or different and the alkyl groups are branched or unbranched.

In particular, it is possible by the process according to the present invention to prepare unsaturated, cyclic orthoesters of the structure 1 where n is from 0 to 4. The value of n includes all values and subvalues therebetween, especially including 0, 1, 2, 3, and 4. Preference is given to preparing, by the process according to the invention, unsaturated compounds of the structure 2

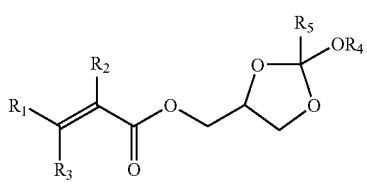

2 where
$R_1$, $R_2$, $R_3$=hydrogen, alkyl or aryl group,
$R_4$=alkyl or aryl group and
$R_5$=hydrogen, alkyl or aryl group, where the alkyl or aryl groups are each substituted or unsubstituted, the substituents of the $R_1$, $R_2$, $R_3$, $R_4$ and/or $R_5$ type are identical or different and the alkyl groups are branched or unbranched.

In the process according to the invention, preference is given to using an unsaturated carboxylic acid of the structure 3

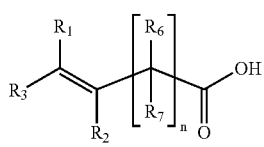

3 where
$R_1$, $R_2$, $R_3$=hydrogen, alkyl or aryl group,
$R_6$, $R_7$=hydrogen or alkyl group and
n=0-10, where the alkyl or aryl groups are each substituted or unsubstituted, the substituents of the $R_1$, $R_2$, $R_3$, $R_6$ and/or $R_7$ type are identical or different and the alkyl groups are branched or unbranched. In the process according to the invention, preference is given to using unsaturated carboxylic acids of the structure 3 where n is from 0 to 4. The value of n includes all values and subvalues therebetween, especially including 0, 1, 2, 3, and 4.

Preference is given to using unsaturated carboxylic acids of the structure 3 where the substituents of the $R_1$, $R_2$, $R_3$, $R_6$ and $R_7$ type are each hydrogen or an alkyl group having a number of carbon atoms of from 1 to 6, but preferably hydrogen or a methyl group. In this case, the alkyl groups of these substituents may be either branched or unbranched, but these substituents are preferably unbranched.

The unsaturated carboxylic acids used in the process according to the present invention are more preferably α,β-unsaturated carboxylic acids of the structure 4

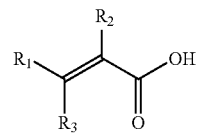

4 where
$R_1$, $R_2$ and $R_3$=hydrogen, alkyl or aryl group, where the alkyl or aryl groups are each substituted or unsubstituted, the substituents of the $R_1$, $R_2$ and/or $R_3$ type are identical or different and the alkyl groups are branched or unbranched.

In particular, the substituents of the $R_1$, $R_2$ and $R_3$ type in the structure 4 are each hydrogen or an alkyl group having a number of carbon atoms of from 1 to 10, preferably from 1 to 6, and more preferably hydrogen or a methyl or ethyl group.

In a particular embodiment of the process according to the invention, the substituent of the $R_3$ type of the α,β-unsaturated carboxylic acid of the structure 4 is hydrogen. The substituents of the R1 and R2 type of the α,β-unsaturated carboxylic acid of the structure 4 are preferably hydrogen or an alkyl group having a number of carbon atoms of from 1 to 6, but preferably hydrogen or a methyl group. In a particularly preferred embodiment of the process according to the invention, the α,β-unsaturated carboxylic acid used is acrylic acid, methacrylic acid or crotonic acid.

In the context of this invention, glycidol is understood to mean the compound 2,3-epoxy-1-propanol.

The process according to the present invention may be carried out in an inert solvent, for example pentane, hexane, cyclohexane, heptane, methylcyclohexane, toluene, benzene, chloroform, methylene chloride, ether, dimethoxyethane, acetone, methyl isobutyl ketone, methanol, ethanol, propanol, butanol, ethylene glycol, glycerol, dimethylformamide, dimethylacetamide.

In particular, the process according to the present invention can be carried out in an inert and halogen-free solvent, for example pentane, hexane, cyclohexane, heptane, methylcyclohexane, toluene, benzene, ether, dimethoxyethane, acetone, methyl isobutyl ketone, methanol, ethanol, propanol, butanol, ethylene glycol, glycerol, dimethylformamide, dimethylacetamide.

However, preference is given to carrying out the process according to the present invention without the use of a solvent. In particular, use is made here of an unsaturated carboxylic acid which is present in liquid form at the reaction temperature of the process according to the invention. Preference is therefore given to using an unsaturated carboxylic acid which has a melting point of not more than 100° C., preferably of not more than 80° C. and more preferably of not more than 50° C. The process according to the present invention can thus be carried out either in a monophasic system or in a biphasic system when the unsaturated carboxylic acid is immiscible with the glycidol at the appropriate reaction temperature.

In a particular embodiment, the unsaturated carboxylic acid is first dissolved or suspended in glycidol; this process is suitable in particular for carboxylic acids which would not be present in liquid form at the reaction temperatures of the process according to the invention.

The process according to the present invention is carried out in the first process stage preferably at a temperature of from 0° C. to 200° C., preferentially from 10° C. to 180° C. and more preferably from 50° C. to 150° C. The temperature includes all values and subvalues therebetween, especially including 10, 20, 30, 40, 50, 60, 70, 80, 90, 100, 110, 120, 130, 140, 150, 160, 170, 180 and 190° C.

The first process stage of the process according to the present invention is carried out preferably at a pressure of from 100 mbar to 50 bar, preferentially at a pressure of from 1 bar to 10 bar and more preferably at atmospheric pressure. The pressure includes all values and subvalues therebetween, especially including 0.2, 0.3, 0.4, 0.5, 0.6, 0.7, 0.8, 0.9, 1, 2, 3, 4, 5, 6, 7, 8, 9, 10, 15, 20, 25, 30, 35, 40 and 45 bar.

The catalyst used in the first process stage of the process according to the present invention may be an acidic catalyst, especially Brønsted or Lewis acids, for example p-toluenesulfonic acid, HCl, $H_3PO_4$, HCOOH, $H_2SO_4$, $NaHSO_4$, oxalic acid, Al(halogen)$_3$, B(halogen)$_3$, $TiCl_4$, $ZnCl_2$, $FeCl_3$, $MgCl_2$. The acidic catalyst used in the first process stage is preferably p-toluenesulfonic acid.

In the first process stage of the process according to the invention, it is also possible to use basic catalysts selected from primary, secondary or tertiary amines; the basic catalysts used are preferably trialkylamines and more preferably triethylamine.

In a particular embodiment of the process according to the invention, a salt-type catalyst is used in the first process stage, especially salts of $NH_3$, or primary, secondary or tertiary amines. The salt-type catalysts used here are preferably $NH_4Cl$, $NEt_3HCl$ or $NBu_3HCl$.

In a further embodiment of the process according to the invention, it is possible in the first process stage to use ion exchangers, especially ion exchangers of the AMBERLYST® type or of the LEWATIT® type. It is likewise possible in the first process stage to use catalysts based on polymer-bound acids, for example MARLON® AS3.

In a particularly preferred embodiment of the process according to the invention, a salt-type catalyst, more preferably $NEt_3HCl$, is used in the first process stage.

In the second process stage of the process according to the invention, preference is given to using an orthoester of the structure 5

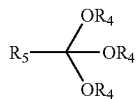

where
$R_4$=alkyl or aryl group,
$R_5$=hydrogen, alkyl or aryl group
is used, where the alkyl or aryl groups are each substituted or unsubstituted, the substituents of the $R_4$ and $R_5$ type are identical or different and the alkyl groups are branched or unbranched. In a particular embodiment of the process according to the invention, orthoesters are used, where two of the substituents of the $OR_4$ type are joined to one another by a hydrocarbon bridge, for example —O—$CH_2$—$CH_2$—O—.

In the process according to the invention, the orthoester used is preferably trialkyl orthoacetate with alkyl groups which have a number of carbon atoms of from 1 to 6. However, preference is given to using orthoesters which have, as substituents of the $R_4$ type, an alkyl group having a number of carbon atoms of from 1 to 4, especially those which have, as substituents of the $R_4$ type, a methyl, ethyl, n-propyl, isopropyl, n-butyl, isobutyl or sec-butyl group. The orthoester used is more preferably trimethyl orthoacetate.

The process according to the present invention is carried out in the second process stage preferably at a temperature of from 0° C. to 200° C., preferably from 10° C. to 100° C. and more preferably from 15° C. to 90° C. The temperature includes all values and subvalues therebetween, especially including 10, 20, 30, 40, 50, 60, 70, 80, 90, 100, 110, 120, 130, 140, 150, 160, 170, 180 and 190° C. In a preferred embodiment of the process according to the invention, the second process stage is carried out at a lower temperature than the first process stage.

The second process stage of the process according to the present invention is carried out preferably at a pressure of from 100 mbar to 50 bar, preferentially at a pressure of from 1 bar to 10 bar and more preferably at atmospheric pressure. The pressure includes all values and subvalues therebetween, especially including 0.2, 0.3, 0.4, 0.5, 0.6, 0.7, 0.8, 0.9, 1, 2, 3, 4, 5, 6, 7, 8, 9, 10, 15, 20, 25, 30, 35, 40 and 45 bar.

The catalyst used in the second process stage of the process according to the present invention may be an acidic or a salt-type catalyst.

The catalyst used in the second process stage of the process according to the present invention may be an acidic catalyst, especially Brønsted or Lewis acids, for example p-toluenesulfonic acid, HCl, $H_3PO_4$, HCOOH, $H_2SO_4$, $NaHSO_4$, oxalic acid, Al(halogen)$_3$, B(halogen)$_3$, $TiCl_4$, $ZnCl_2$, $FeCl_3$, $MgCl_2$. The acidic catalyst used in the second process stage is preferably p-toluenesulfonic acid.

In a particular embodiment of the process according to the invention, a salt-type catalyst is used in the second process stage, especially salts of $NH_3$, or primary, secondary or tertiary amines. The salt-type catalysts used here are preferably $NH_4Cl$, $NEt_3HCl$ or $NBu_3HCl$.

In a further embodiment of the process according to the invention, it is possible in the second process stage to use ion exchangers, especially ion exchangers of the AMBERLYST® type or of the LEWATIT® type. It is likewise possible in the second process stage to use catalysts based on polymer-bound acids, for example MARLON® AS3.

In a particular embodiment of the process according to the invention, different catalysts are used for the two process stages; in this context, particular preference is given to using a basic catalyst, especially triethylamine, in the first process stage, and an acidic catalyst, especially p-toluenesulfonic acid, in the second process stage. In the process according to the invention, it is, however, also possible to use one and the same catalyst for both process stages, so that it is possible to dispense with an additional catalyst addition in the second process stage. For this purpose, preference is given to using an acidic or a salt-type catalyst for both process stages.

The two process stages of the process according to the present invention may be carried out in the same reactor without workup of intermediates being necessary.

Both the first and second process stage of the process according to the present invention may be carried out continuously or batchwise.

In the process according to the invention, preference is given to initially charging the unsaturated carboxylic acid and to adding the further reactants gradually, especially to adding them dropwise, for example the glycidol in the first process stage or the orthoesters of the structure 3 in the second process stage. The reactants may be added dropwise over several hours.

When the glycidol serves as a solvent or suspension medium for the unsaturated carboxylic acid, the dropwise addition in the first process stage may be partly or entirely dispensed with.

After the second process stage, the reaction mixture may be freed of low boilers present in the reaction mixture by means of a distillation. Subsequently, the product can be purified by means of a vacuum distillation.

Having generally described this invention, a further understanding can be obtained by reference to certain specific examples which are provided herein for purposes of illustration only, and are not intended to be limiting unless otherwise specified.

EXAMPLES

The examples which follow are intended to illustrate the process according to the invention for preparing unsaturated, cyclic orthoesters in detail without the invention being restricted to this embodiment.

Example 1

115 g of acrylic acid and 7.7 g of triethylamine hydrochloride were initially charged in a round-bottom flask together with 0.7 g of hydroquinone and heated to 85° C. 120 g of glycidol were added dropwise to this reactant mixture and the resulting solution was stirred at 85° C. for 0.5 hour. The reaction mixture was subsequently cooled to 75° C. 85 g of trimethyl orthoacetate were added dropwise to this reaction mixture, which was subsequently stirred at 70° C. for 1 hour. The reaction mixture was then freed of the low boilers present by means of a distillation. Subsequently, a vacuum distillation was carried out at 4 mbar and 95° C. 4-Acryloyloxymethyl-2-methoxy-2-methyl-1,3-dioxolane was obtained in a yield of 85%.

Example 2

47 g of acrylic acid and 3.04 g of p-toluenesulfonic acid were initially charged in a round-bottom flask together with 0.2 g of hydroquinone and heated to 104° C. 40 g of glycidol were added dropwise to this reactant mixture and the resulting solution was stirred at 100° C. for 45 minutes. Subsequently, the reaction mixture was cooled to 25° C. 84 g of trimethyl orthoacetate were added dropwise to this reaction mixture, which was subsequently stirred at 25° C. for one hour. The reaction mixture was then freed of the low boilers present by means of a distillation. Subsequently, a vacuum distillation was carried out at 4 mbar and 95° C. 4-Acryloyloxymethyl-2-methoxy-2-methyl-1,3-dioxolane was obtained in a yield of 56%.

Example 3

47 g of acrylic acid and 1.62 g of triethylamine were initially charged in a round-bottom flask together with 0.2 g of hydroquinone and heated to 70° C. 40 g of glycidol were added dropwise to this reactant mixture and the resulting solution was stirred at 70° C. for 45 minutes. Subsequently, the reaction mixture was cooled to 25° C. 3 g of p-toluenesulfonic acid were added to this reaction mixture, then 84 g of trimethyl orthoacetate were added dropwise and the mixture was subsequently stirred at 25° C. for one hour. The reaction mixture was then freed of the low boilers present by means of a distillation. Subsequently, a vacuum distillation was carried out at 4 mbar and 95° C. 4-Acryloyloxymethyl-2-methoxy-2-methyl-1,3-dioxolane was obtained in a yield of 45%.

Example 4

Glycidol and acrylic acid which comprises 6.4% by weight of triethylamine hydrochloride and 0.6% by weight of hydroquinone were metered together into a loop reactor heated to 125° C. The metering rate for glycidol was 40 g/h; that for the acrylic acid/hydroquinone/catalyst solution was 41 g/h. The residence time was approx. 15 min. The effluent of the loop reactor within one hour was collected, cooled and admixed with 69 g of trimethyl orthoacetate. The mixture was stirred at 25° C. for 1 hour. A crude product of the 4-acryloyloxymethyl-2-methoxy-2-methyl-1,3-dioxolane was obtained in a yield of 63% by GC analysis.

German patent application 10 2005 018 909.1 filed Apr. 22, 2005, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A process for preparing an unsaturated, cyclic orthoester, comprising:
    in a first process stage, reacting an unsaturated carboxylic acid with glycidol, thereby obtaining a reaction mixture; and
    in a second process stage, adding an orthoester to the reaction mixture, thereby obtaining said unsaturated, cyclic orthoester.

2. The process as claimed in claim 1, wherein an unsaturated carboxylic acid of the following structure is used

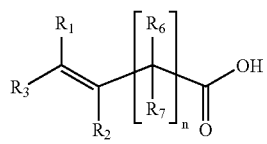

wherein
$R_1$, $R_2$, $R_3$=hydrogen, alkyl or aryl group,
$R_6$, $R_7$=hydrogen or alkyl group, and
n=0-10,
wherein the alkyl or aryl groups are each substituted or unsubstituted, $R_1$, $R_2$, $R_3$, $R_6$ and/or $R^7$ are identical or different and the alkyl groups are branched or unbranched.

3. The process as claimed in claim 2, wherein the unsaturated carboxylic acid used is an α,β-unsaturated carboxylic acid of the following structure

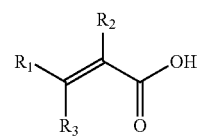

wherein
R₁, R₂ and R₃=hydrogen, alkyl or aryl group,
wherein the alkyl or aryl groups are each substituted or unsubstituted, R₁, R₂ and/or R₃ are identical or different and the alkyl groups are branched or unbranched.

4. The process as claimed in claim 3, wherein the α,β-unsaturated carboxylic acid is acrylic acid, methacrylic acid or crotonic acid.

5. The process as claimed in claim 1, wherein the first process stage is carried out at a temperature of from 50° C. to 150° C.

6. The process as claimed in claim 1, wherein the same catalyst is used for both process stages.

7. The process as claimed in claim 6, wherein an acidic catalyst is used.

8. The process as claimed in claim 6, wherein a salt catalyst is used.

9. The process as claimed in claim 1, wherein different catalysts are used for the two process stages.

10. The process as claimed in claim 9, wherein a basic catalyst is used in the first process stage and an acidic catalyst in the second process stage.

11. The process as claimed in claim 1, wherein, in the second process stage, an orthoester of the following structure is used

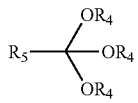

wherein
R₄=alkyl or aryl group, and
R₅=hydrogen, alkyl or aryl group,
wherein the alkyl or aryl groups are each substituted or unsubstituted, R₄ and R₅ are identical or different and the alkyl groups are branched or unbranched.

12. The process as claimed in claim 1, wherein both process stages are carried out in the same reactor.

13. The process as claimed in claim 1, which is carried out without the isolation and workup of an intermediate.

14. The process as claimed in claim 1, which is carried out without the presence of a solvent.

15. The process as claimed in claim 1, which is carried out without the presence of a halogenated compound.

16. The process as claimed in claim 1, wherein said unsaturated, cyclic orthoester has the following structure

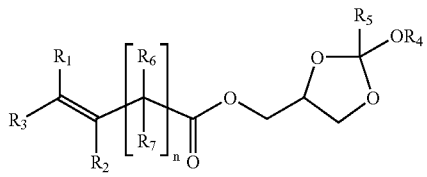

wherein
R₁, R₂, R₃=hydrogen, alkyl or aryl group,
R₄=alkyl or aryl group,
R₅=hydrogen, alkyl or aryl group,
R₆, R₇=hydrogen or alkyl group, and
n=0-10,
wherein the alkyl or aryl groups are each substituted or unsubstituted, R₁, R₂, R₃, R₄, R₅, R₆ and/or R₇ are identical or different and the alkyl groups are branched or unbranched.

17. The process as claimed in claim 16, wherein n is from 0 to 4.

18. The process as claimed in claim 1, wherein said unsaturated, cyclic orthoester has the following structure

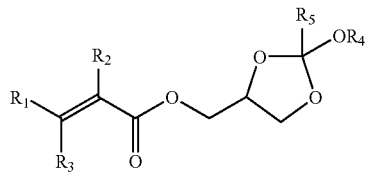

wherein
R₁, R₂, R₃=hydrogen, alkyl or aryl group,
R₄=alkyl or aryl group, and
R₅=hydrogen, alkyl or aryl group,
wherein the alkyl or aryl groups are each substituted or unsubstituted, R₁, R₂, R₃, R₄ and/or R₅ are identical or different and the alkyl groups are branched or unbranched.

19. The process as claimed in claim 1, which is carried out in an inert solvent.

20. The process as claimed in claim 1, further comprising removing low boilers from the reaction mixture, and distilling the unsaturated, cyclic orthoester.

* * * * *